US00PP33034P2

(12) United States Plant Patent
Scheffers

(10) Patent No.: US PP33,034 P2
(45) Date of Patent: May 4, 2021

(54) ***DRACAENA* PLANT NAMED 'DRA201901'**

(50) Latin Name: *Dracaena fragrans*
Varietal Denomination: DRA201901

(71) Applicant: Dragontree Beheer B.V., Honselersdijk (NL)

(72) Inventor: Ruud Scheffers, Honselersdijk (NL)

(73) Assignee: Dragontree Beheer B.V., Honselersdijk (NL)

( * ) Notice: Subject to any disclaimer, the term of this patent is extended or adjusted under 35 U.S.C. 154(b) by 0 days.

(21) Appl. No.: 16/895,374

(22) Filed: Jun. 8, 2020

(51) Int. Cl.
*A01H 6/12* (2018.01)
*A01H 5/00* (2018.01)

(52) U.S. Cl.
USPC ..... Plt./383

(58) Field of Classification Search
USPC ..... Plt./383
See application file for complete search history.

*Primary Examiner* — Annette H Para
(74) *Attorney, Agent, or Firm* — Samuel R. McCoy, Jr.

(57) ABSTRACT

A new and distinct *Dracaena* plant named 'DRA201901' which is characterized by an abundance of foliage born on an unbranched stem, glossy green foliage with broad yellow-green margins, foliage that is slightly to moderately spiraled and distally curled downward, coarsely undulate foliar margins, and the stability of these characteristics from generation to generation.

2 Drawing Sheets

Latin name of the genus and species: The Latin name of the genus and species of the novel variety disclosed herein is *Dracaena fragrans.*

Variety denomination: The inventive cultivar of *Dracaena* disclosed herein has been given the variety denomination 'DRA201901'.

BACKGROUND OF THE INVENTION

Parentage: 'DRA201901' is a spontaneous branch-plant mutation of a *Dracaena fragrans* '004027J' (not patented) which was discovered at a commercial greenhouse in Honselersdijk, the Netherlands in the summer of 2010. The mutation was initially noted for its abundant foliage with narrow yellow leaf margins. Said mutation was isolated for further evaluation to confirm the uniformity and stability of the unique characteristics first observed. Upon confirmation of the stability and uniformity of the characteristics, the new plant was selected for commercialization.

Asexual Reproduction: Asexual reproduction of 'DRA201901' is accomplished by way of rooting stem cuttings. Propagation was first performed in the summer of 2010 at the inventor's commercial greenhouse in Honselersdijk, the Netherlands. Through eight subsequent generations, the unique features of this cultivar have proven to be stable and true to type.

SUMMARY OF THE INVENTION

The cultivar 'DRA201901' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'DRA201901'. These characteristics in combination distinguish 'DRA201901' as a new and distinct *Dracaena fragrans* cultivar:

1. *Dracaena* 'DRA201901' exhibits an abundance of foliage born on an unbranched stem; and 2. *Dracaena* 'DRA201901' exhibits foliage that is slightly to moderately spiraled and distally curled downward; and
3. *Dracaena* 'DRA201901' exhibits foliage with coarsely undulate margins; and
4. *Dracaena* 'DRA201901' exhibits glossy dark green foliage with broad yellow-green margins.

BOTANICAL DESCRIPTION OF THE PLANT

Figure 1:
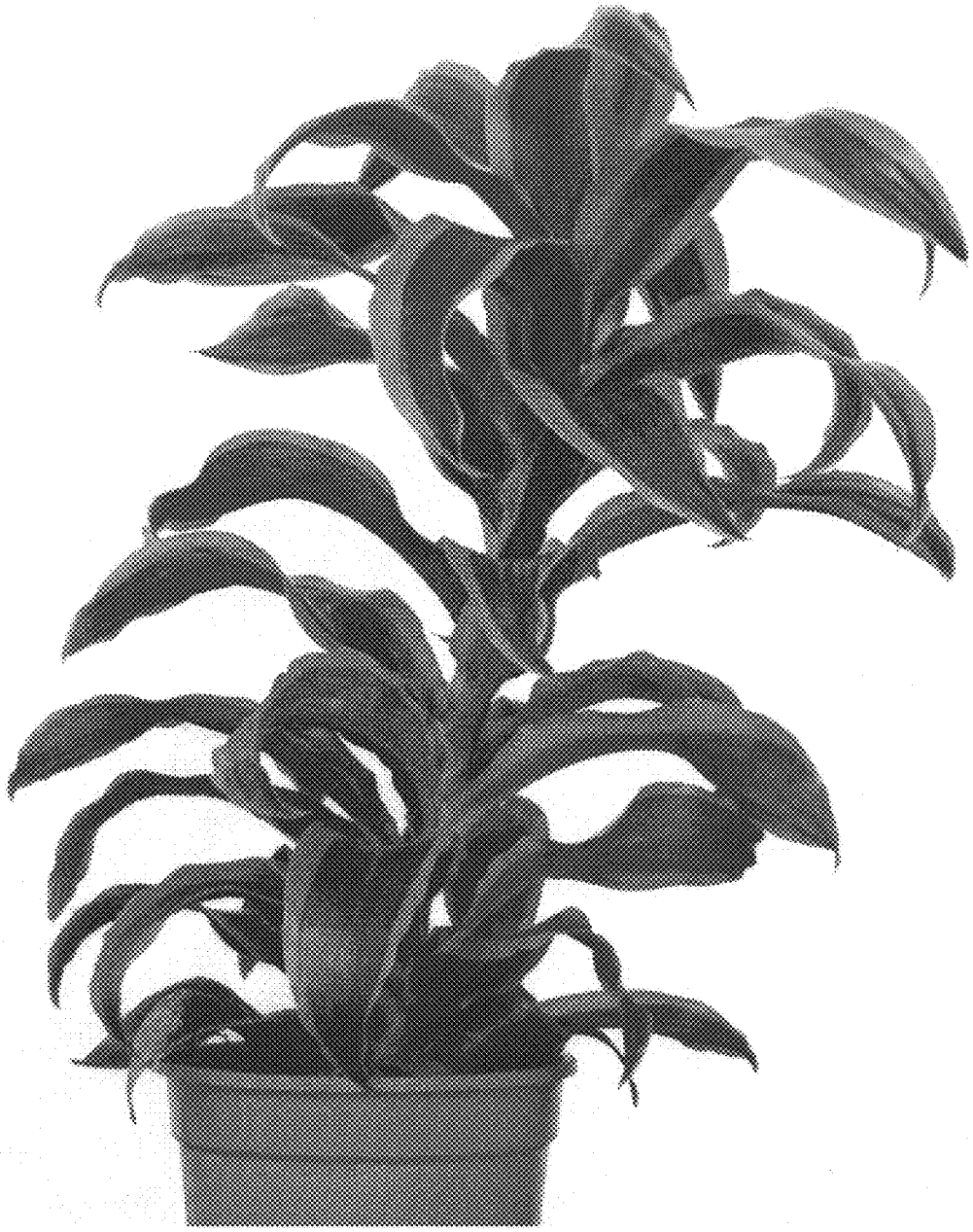
FIG. 1 illustrates, as nearly true as it is reasonably possible to make the same in color photographs of this type, an exemplary plant of 'DRA201901' grown in Honselersdijk, the Netherlands. This plant, grown in a 11 cm nursery container, is approximately 16 weeks old from a rooted young plant.
Figure 2:
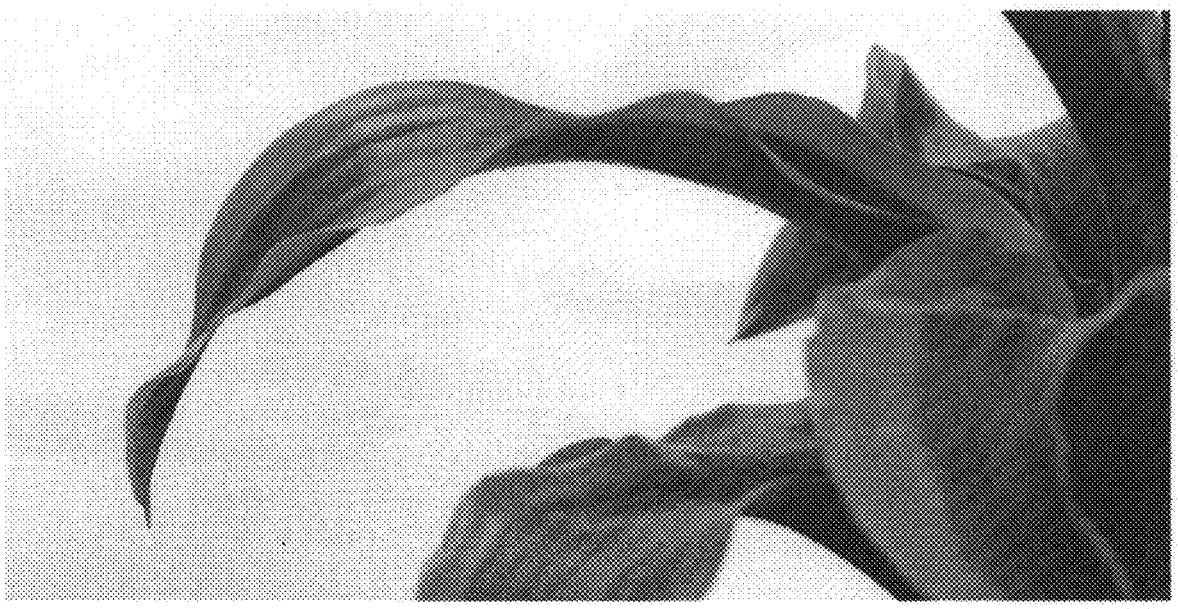
FIG. 2 illustrates, as nearly true as it is reasonably possible to make the same in color photographs of this type, the typical foliage of 'DRA201901'.

The following observations and measurements, made in May of 2020, describe averages from a sample set of six specimens of 12 week-old 'DRA201901' plants grown in 15 cm nursery pots in Honselersdijk, the Netherlands. Plants were produced using conventional greenhouse production protocols for *Dracaena* sp. which consisted of growing under shade, regular overhead irrigation and regular fertigation, and chemical control of thrips insects. No photoperiodic treatments or artificial light was given to the plants.

Those skilled in the art will appreciate that certain characteristics will vary with older or, conversely, with younger plants. 'DRA201901' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'DRA201901' and comparisons with the parent plant and most similar commercial *Dracaena* cultivar known to the inventor are provided below.

Plant description:

*Growth habit.*—Evergreen perennial with foliage born on a solitary upright, unbranched stem.

*Plant profile.*—Oblong.

*Height.*—14.7 cm.

*Width.*—Average of 38.3 cm.

*Growth rate.*—Moderately fast to fast growing.

*Plant vigor.*—Highly vigorous.

*Propagation.*—Method — Asexual propagation is accomplished by stem cuttings. Time to initiate jroots — Approximately 30 days are required to initiate roots at 20 degrees Celsius. Time to produce a marketable 12 cm potted plant — Approximately 12 to 16 weeks. Pinching will increase lateral branching.

*Disease and pest resistance or susceptibility.*—Neither tolerance nor resistance to normal diseases and pests of *Dracaena fragrans* have been observed.

*Environmental tolerances.*—Adapt to USDA Hardiness Zones 10 through 12 and temperatures as high as 40 degrees Celsius; moderate tolerance to rain and wind.

Root system:

*General.*—Fibrous; freely branched and moderately dense rooting.

*Distribution in the soil profile.*—Shallow to moderately deep.

*Texture.*—Smooth; glabrous.

*Color.*—Greyed-orange, RHS N170A.

Stems:

*Branching characteristics.*—Not freely branched in nature; develops lateral branches only when manipulated by man by way of pruning. Naturally produces one main stem arising from the plant's base.

*Attitude.*—Near vertical.

*Strength.*—Very strong.

*Length.*—36.0 cm.

*Diameter.*—Average 1.5 cm.

*Internode length.*—Average 1.3 cm.

*Stem texture.*—Glabrous; smooth.

*Stem luster.*—Slightly glossy.

*Color, developing stems.*—Yellow-green, nearest to RHS 145B.

*Color, mature stems.*—Yellow green, nearest to a mixture of RHS 145B and in between RHS 146A and 147A.

*Color at the internodes.*—Yellow green, nearest to in between RHS 146A and 147A.

Foliage:

*Arrangement.*—Spiraled.

*Attachment.*—Sheathed.

*Division.*—Simple.

*Attitude.*—Foliage near the apex is held upright to outward and becomes progressively more relaxed towards the base.

*Number of leaves per lateral branch.*—42.

*Lamina.*—Dimensions — 21.6 cm long and 6.4 cm wide, on average. Shape — Lorate. Aspect — Slightly to moderately axially twisted (i.e. spiraled); distal portion on the lamina pointing downward at an average angle of minus-60 degrees to the rest of the lamina. Apex — Acute with a short, soft but pointed tip. Base — Sheathed. Sheath Length — 2.4 cm. Width — 4.5 cm. Color, adaxial surface — Green-white, nearest to RHS 157A. Color, abaxial surface — Yellow-green, nearest to RHS 147A, and suffused with green, nearest to RHS 139A. Margin — Entire; coarsely undulate. Texture and luster of adaxial surface — Smooth, glabrous and moderately glossy. Texture and luster of abaxial surface — Smooth, glabrous and moderately glossy. Color — Juvenile foliage, adaxial surface — In between yellow-green and green, nearest to RHS 143A and 146A, but darker; broadly margined yellow-green, nearest to in between RHS N144A and 150A. Juvenile foliage, abaxial surface — Green, nearest to RHS 143A, and margined yellow-green, nearest to RHS N144A. Mature foliage, adaxial surface — Green, nearest to in between RHS NN137A and 139A, but slightly darker; irregularly margined yellow-green, nearest to RHS 144B. Mature foliage, abaxial surface — Green, nearest to RHS 143A, but darker; irregularly margined yellow-green, nearest to RHS 144B. Venation — Pattern — Parallel. Color, adaxial surface — The main vein nearest green, nearest to RHS 137A. All other veins are indistinguishable from the surrounding foliage: green, nearest to in between RHS NN137A and 139A, and irregularly margined yellow-green, nearest to RHS 144B. Color, abaxial surface — The main vein is green, nearest to RHS 143B. All other veins are indistinguishable from the surrounding foliage: green, nearest to RHS 143A, and irregularly margined yellow-green, nearest to RHS 144B.

Inflorescence: To date, flowering has not been observed.

Flower buds: To date, flowering has not been observed.

Flower: To date, flowering has not been observed.

Reproductive organs: To date, flowering has not been observed.

Seed and fruit: To date, flowering has not been observed.

Comparisons with the Parent Plant

Plants of the new cultivar 'DRA201901' may be distinguished from its parent, *Dracaena fragrans* '004027J' (not patented), by the characteristics described in Table 1.

TABLE 1

| Characteristic | 'DRA201901' | '004027J' |
|---|---|---|
| Foliage aspect. | More spiralled. | Less spiralled. |
| Base color of the foliage. | Lighter green by comparison to '004027J'. | Darker green by comparison to 'DRA201901'. |
| Foliage margin coloration. | More broadly margined yellow-green. | More narrowly margined yellow-green. |

Plants of the new cultivar 'DRA201901' may be distinguished from the closest known commercial comparator, *Dracaena fragrans* 'DRADORCO' (U.S. Plant Pat. No. 27,785), by the characteristics described in Table 2.

TABLE 2

| Characteristic | 'DRA201901' | 'Dradorco' |
|---|---|---|
| Growth habit. | Less compact than 'Dradorco'. | More compact than 'DRA201901'. |
| Foliage aspect. | More spiralled. | Less spiralled. |

TABLE 2-continued

| Characteristic | 'DRA201901' | 'Dradorco' |
|---|---|---|
| Base color of the foliage. | Lighter green by comparison to '004027J'. | Darker green by comparison to 'DRA201901'. |
| Foliage margin coloration. | Lighter yellow-green by comparison to '004027J'. | Darker yellow-green by comparison to 'DRA201901'. |

That which is claimed is:

1. A new and distinct cultivar of *Dracaena* plant named 'DRA201901', substantially as described and illustrated herein.

* * * * *